United States Patent
Pai et al.

[11] Patent Number: 6,156,267
[45] Date of Patent: *Dec. 5, 2000

[54] APPARATUS AND METHOD FOR REAL-TIME MONITORING AND CONTROL OF ANTI-MICROBIAL PROCESSING

[75] Inventors: Sanjeeth M. Pai, Rocky Mount; Peter E. Zell, Raleigh, both of N.C.

[73] Assignee: Steris Corporation, Mentor, Ohio

[*] Notice: This patent is subject to a terminal disclaimer.

[21] Appl. No.: 09/123,113

[22] Filed: Jul. 27, 1998

Related U.S. Application Data

[63] Continuation-in-part of application No. 08/602,515, Feb. 16, 1996, Pat. No. 5,788,925.

[51] Int. Cl.[7] .................................................. G05B 13/00
[52] U.S. Cl. ........................... 422/3; 422/28; 422/37; 422/116; 422/119; 422/292
[58] Field of Search .................... 422/3, 28, 37, 422/116, 119, 292; 73/865.9; 374/142, 143

[56] References Cited

U.S. PATENT DOCUMENTS

| | | |
|---|---|---|
| 3,861,875 | 1/1975 | Joslyn . |
| 3,982,893 | 9/1976 | Joslyn . |
| 4,067,691 | 1/1978 | McGady et al. . |
| 4,164,538 | 8/1979 | Young et al. . |
| 4,203,947 | 5/1980 | Young et al. . |
| 4,261,950 | 4/1981 | Bainbridge et al. . |
| 4,309,381 | 1/1982 | Chamberlain et al. . |
| 4,594,223 | 6/1986 | Dyke et al. . |
| 4,687,635 | 8/1987 | Kaehler et al. . |
| 4,839,291 | 6/1989 | Welsh et al. . |
| 4,914,034 | 4/1990 | Welsh et al. . |
| 5,164,161 | 11/1992 | Feathers et al. . |
| 5,229,072 | 7/1993 | Tarancon ................................... 422/37 |
| 5,258,921 | 11/1993 | Ellis . |
| 5,270,948 | 12/1993 | O'Brien et al. . |
| 5,290,511 | 3/1994 | Newman . |
| 5,340,537 | 8/1994 | Barrett . |
| 5,368,821 | 11/1994 | Schmoegner et al. . |
| 5,380,485 | 1/1995 | Takahashi et al. . |
| 5,390,322 | 2/1995 | O'Brien et al. . |
| 5,413,757 | 5/1995 | Kutner et al. . |
| 5,422,276 | 6/1995 | Colvin . |
| 5,426,428 | 6/1995 | Binder et al. . |
| 5,478,749 | 12/1995 | Dyke . |
| 5,491,092 | 2/1996 | Colvin . |
| 5,565,634 | 10/1996 | Graessle et al. . |
| 5,788,925 | 8/1998 | Pai et al. ...................................... 422/3 |

FOREIGN PATENT DOCUMENTS

| | | |
|---|---|---|
| 2427834A1 | 1/1975 | Germany . |
| 0604387A1 | 6/1994 | Germany . |
| 9319369 | 4/1995 | Germany . |
| WO93/21964 | 11/1993 | WIPO . |
| WO95/32742 | 12/1995 | WIPO . |
| WO 9729789 | 8/1997 | WIPO . |
| WO 9800176 | 1/1998 | WIPO . |

OTHER PUBLICATIONS

ISO/TC 198/WG 3, Feb. 1995, 5.2.5, International Organization For Standardization.

*Primary Examiner*—Terrence R. Till
*Assistant Examiner*—Theresa T. Snider
*Attorney, Agent, or Firm*—Fay, Sharpe, Fagan, Minnich & McKee, LLP

[57] ABSTRACT

The present invention provides a system and method for real-time monitoring and control of anti-microbial cycle parameters within a load-simulation device 6. The system and method simulate the same conditions as those within an acceptable standard challenge load to be sterilized. Integration of the system into a control system 17 allows critical anti-microbial parameter levels to be achieved and maintained within the simulated load throughout a cycle, thus resulting in a significant reduction in the number of unsuccessful cycles. A redundant parameter-monitoring system 100 within the system is included. When acceptable parameter levels are shown to have been met, the processed load is automatically released for use immediately upon completion of the cycle, thus eliminating the need for biological indicators and chemical integrators.

20 Claims, 7 Drawing Sheets

TO PARAMETER
CONTROL MEANS
100

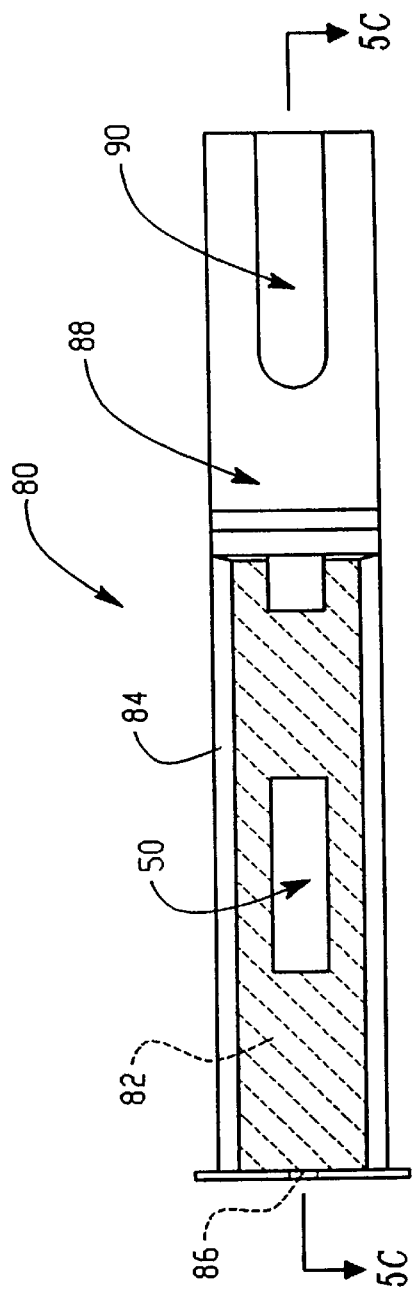
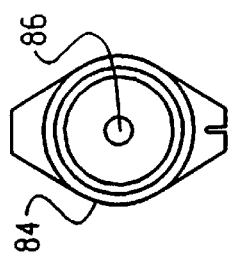
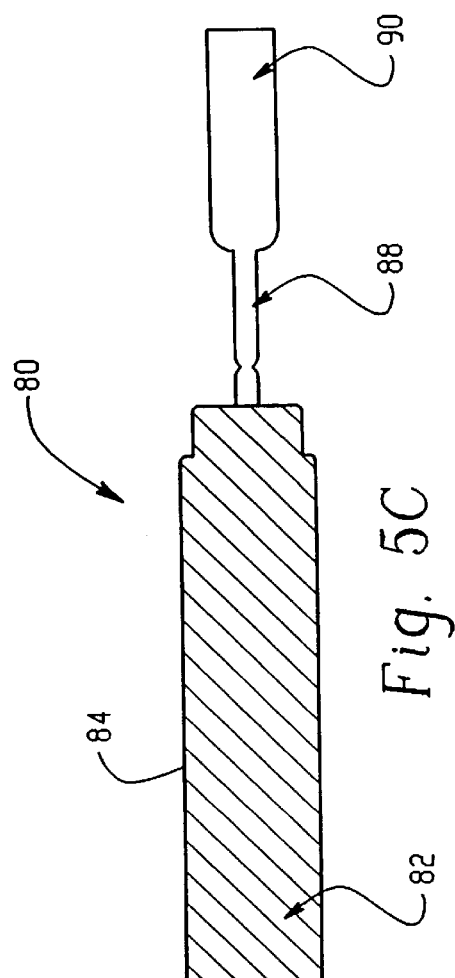

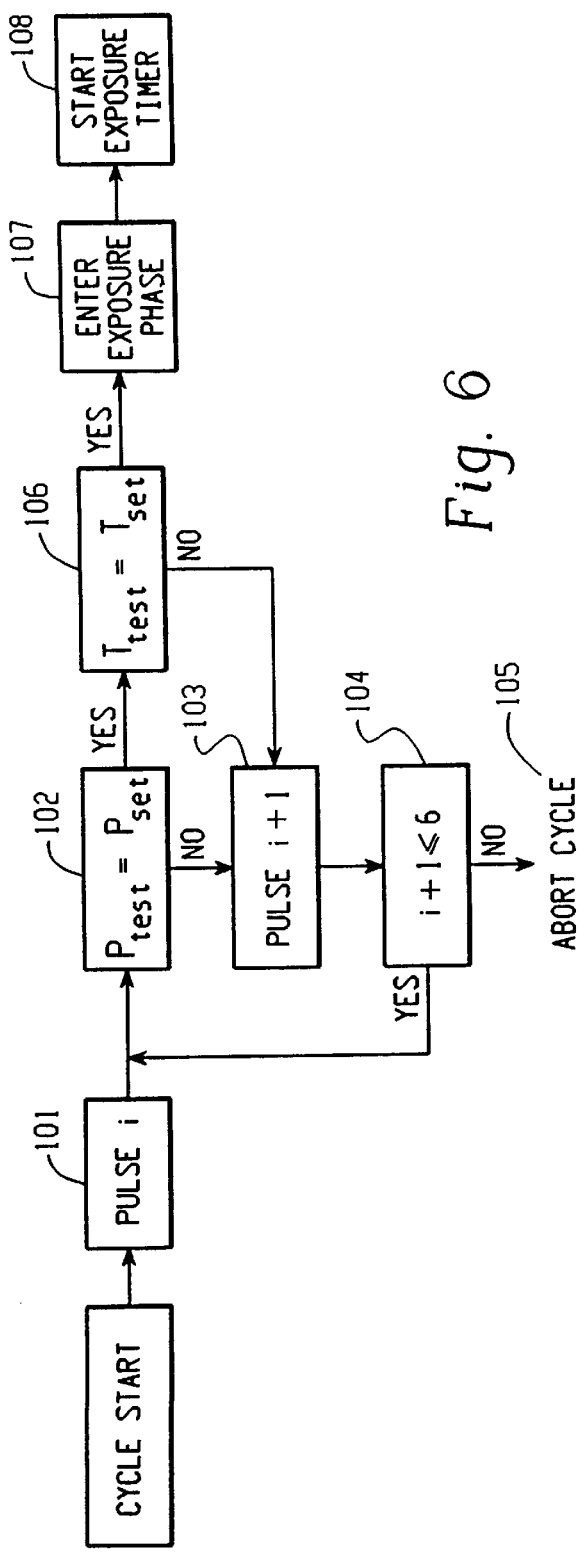
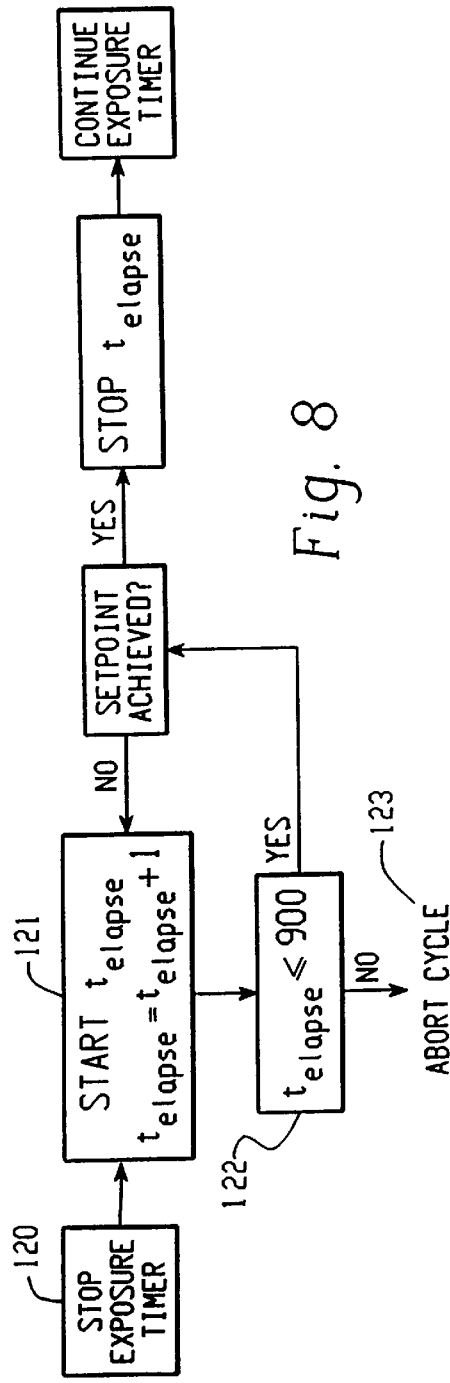
Fig. 6
Fig. 8

APPARATUS AND METHOD FOR REAL-TIME MONITORING AND CONTROL OF ANTI-MICROBIAL PROCESSING

CROSS-REFERENCES TO RELATED APPLICATIONS

The present application is a continuation-in-part application of U.S. patent application Ser. No. 08/602,515 filed on Feb. 16, 1996, now U.S. Pat. No. 5,788,925.

BACKGROUND OF THE INVENTION

Monitoring of sterilization parameters is essential to ensure that optimum sterilizing conditions during a steam or chemical sterilization cycle are met. Environmental conditions in the chamber are frequently measured by various sensors, such as temperature, pressure, or sterilant concentration sensors, positioned in strategic places, such as a chamber wall or a drain line. The sensors, in turn, may be connected by various methods (e.g. electrical, radio transmitter, etc.) to an integral or remote microprocessor controller programmed to monitor and respond to the sensor readings and provide control of critical cycle parameters in the chamber, such as temperature, pressure, relative humidity, sterilant concentration and time during the cycle.

Control of cycle parameters in the chamber, however, does not guarantee that sterilization conditions have been met within the load to be sterilized. Systems have been developed employing temperature and pressure sensors placed within an actual load or in standardized devices simulating a load. Each of these prior systems has disadvantages. For example, a sensor placed in an actual load monitors a condition only at the sensor location and does not necessarily reflect the condition elsewhere in the load. Load simulation devices, such as those containing a heat sink to detect the presence of air or superheated steam or those containing sensors to monitor and record time, temperature, pressure and/or moisture, have the disadvantage that the load-simulation devices are not integrated with the sterilizer control system and are monitors only. In some, information is available only after the sterilization cycle, when the device is removed from the chamber and the record of a parameter is interpreted visually (e.g. a color change) by the operator. In others, the monitored information is transmitted to an external stand alone control and display unit, adding to the expense of a sterilization system. Neither approach provides the capability of real-time monitoring of critical load parameters with direct and simultaneous conveyance of the information to the sterilizer control system allowing real-time control of critical sterilization parameter levels within the load. Further, prior load-simulation devices monitor only such parameters as temperature, pressure, time, moisture or the presence of a sterilant. They do not provide the capability of also directly monitoring the concentration of a chemical sterilant, such as ethylene oxide gas or hydrogen peroxide liquid or vapor, in a load, or of directly conveying the results to the sterilization control for real-time control of the sterilant concentration in the load.

Currently, the Association for Advancement of Medical Instrumentation (AAMI) guidelines recommend that chemical integrators and biological indicators be used to verify that process parameters critical for sterilization have been achieved. Chemical integrators provide a visual indication (e.g. a color change) that predetermined sterilization parameters were presumably achieved. For example, in the case of steam or ethylene oxide sterilization, a chemical integrator might indicate that a given temperature with the presence of moisture was achieved for a given time. Chemical integrators, however, are not sophisticated enough to monitor critical cycle parameters (e.g. temperature, pressure, sterilant concentration) to a confidence level that would assure that sterilization has occurred and to allow release of the load for use based on the indicator results alone. Therefore, biological indicators are additionally employed. Presumably, if proper conditions in the chamber with respect to time, temperature, pressure and/or sterilant concentration are achieved and maintained for the required exposure period, the biological agent in the indicator will be killed, and thereby indicate cycle efficacy. However, the requirement for a sometimes lengthy incubation of the biological indicator to assure confirmation of sterility can result in an undesirable time delay after cycle completion before the sterilization efficacy is known. This delay can significantly affect productivity and, therefore, the cost of processing goods through the sterilization system, in addition to the inconvenience of delayed turnaround of critical medical or dental instruments.

Recently, the concept of parametric release has been described for moist heat sterilization, and seeks to provide a more efficient means for monitoring a steam sterilization process. Parametric release is based on the physical monitoring in the chamber of the parameters of pressure, temperature and rate of change of temperature and pressure during the moist heat sterilization cycle. The chamber control is set for a predetermined cycle, to achieve and maintain predetermined critical parameter levels for a given period of time. The chamber parameters are monitored throughout the cycle. If the monitoring indicates a difference between a set and measured parameter value that exceeds specified limits, a warning is given to the cycle operator. If the monitoring indicates that the critical levels in the chamber are achieved and maintained for the time required to achieve a given sterility assurance level, the cycle is considered efficacious and the load is released for use. Therefore, parametric release systems are designed to provide monitoring and notification only of achieved parameters in the chamber. They do not suggest providing real-time sensing data to the sterilizer control system to enable the sterilizer control to react to changes in the critical parameters and adjust them in order to avoid unsuccessful cycles. Rather, current International Organization For Standardization (ISO) and European Committee for Standardization (CEN) standards require that the monitoring system for parametric release be separate from the sterilizer control system. Further, the process is described only for control of parameters in the chamber and does not address the monitoring and control of the critical parameter levels in the load itself.

A need exists, therefore, for a sterilization system that provides both real-time monitoring and real-time control of critical sterilization parameters in the load, to a sterility assurance level that eliminates the need for chemical and biological indicators. Moreover, there is a need for a device that provides real-time monitoring of critical sterilization parameters in the load, and is also integrated with the sterilizer control system to enable the control to react to monitored changes in the critical parameter levels and adjust them in real-time in order to avoid unsuccessful cycles. Additionally, there is a need for a device that reproducibly simulates a standard challenge load undergoing sterilization and that contains critical parameter sensors that are directly integrated into the sterilizer control system. Furthermore, there is a need for a sterilization system that provides for the release of a load when the critical values of sterilization parameters in the load are shown to have been met.

SUMMARY OF THE INVENTION

The present invention provides real-time monitoring and control of anti-microbial processing cycle parameters, within a load-simulating device that simulates the same conditions as those which would be found in an acceptable standard challenge load to be processed. The levels of critical load processing parameters, such as temperature, pressure, relative humidity, and anti-microbial agent concentration are sensed by sensor probes positioned within the load-simulating device and the data transmitted directly, in real-time, to the control system. The control system then provides real-time control of critical parameter levels within the simulated load device.

A redundant set of sensor probes within the device also monitors the anti-microbial processing parameters in real-time and transmits the sensed data to a parametric release monitoring system. If the monitored parameter levels indicate anti-microbial cycle efficacy (as measured by the conditions sensed within the load-simulating device), the load is released for use immediately upon completion of the cycle. Thus, the present invention eliminates the need for chemical integrators and biological indicators and increases the efficiency of anti-microbial processing.

In one aspect, the present invention provides an apparatus for improving real-time control of an anti-microbial processing cycle. The apparatus comprises a challenge load-simulating device having a resistance barrier that is resistant to penetration of an anti-microbial agent and a receiving chamber for the anti-microbial agent that penetrates the resistance barrier. The apparatus further comprises a sensing element disposed in the receiving chamber of the challenge load-simulating device that provides a real-time control signal.

In yet another aspect, the present invention provides a system for monitoring and controlling an anti-microbial processing cycle. The system comprises a challenge load-simulating device, a sensor positioned in the receiving area for real-time sensing therein of an anti-microbial processing parameter value during an anti-microbial processing cycle. The system further comprises a control system for controlling the value of the parameter in real time during the cycle. The system also comprises a first transmitting element in communication with the sensor for transmitting the sensed parameter value from the sensor to the control system.

In still a further aspect, the present invention provides a challenge load-simulating device comprising a semi-permeable barrier that is characterized by being resistant to penetration of an anti-microbial agent and having a certain configuration. The device also comprises a receiving area for the anti-microbial agent that penetrates the resistance barrier. A sensor probe is disposed in the receiving area for real-time sensing therein of an anti-microbial processing parameter.

In yet another aspect, the present invention provides a method for monitoring and controlling a parameter value in a simulated load during an anti-microbial process performed in a decontamination apparatus. The method comprises positioning a challenge load-simulating device in the apparatus. A sensor probe is placed within the device for real-time sensing therein of a parameter value during the anti-microbial process. The load-simulating device is then exposed to the anti-microbial agent during the anti-microbial process. The method then involves sensing the parameter value within the receiving area of the device during the process and transmitting the sensed parameter value in the device from the sensor to the control system. The method also involves a step of controlling the value of the parameter in real time during the process in response to a signal from the control system.

The present invention further provides, in yet another aspect, a method of monitoring and controlling a parameter value in a simulated load during an anti-microbial processing cycle performed in a decontamination apparatus. The method comprises placing a particular challenge load-simulating device in the decontamination apparatus, exposing the device to anti-microbial agent during the cycle, and sensing the parameter value within the receiving area of the device. The sensed parameter value is transmitted to a control system which controls temperature, pressure, humidity, and/or anti-microbial agent concentration in real time during the cycle in response to the sensed parameter value.

Moreover, the present invention provides in a further aspect, a method of monitoring and controlling a parameter value in a simulated load during an anti-microbial cycle in a decontamination apparatus having a control system programmed in a particular fashion. The method involves positioning a challenge load-simulating device in the apparatus and placing a sensor probe in the device for real-time sensing of a parameter during the cycle. The device is exposed to an anti-microbial agent selected from an array of agents. The parameter value in the device is sensed and transmitted to the control system. The method also involves controlling the value of the parameter in real time based upon a comparison of the sensed parameter value to a predetermined parameter range stored in the control system.

Still further, in yet another aspect, the present invention provides a method for monitoring and controlling an anti-microbial process in a decontamination chamber by placing a particular load-simulating device in the chamber and conducting an anti-microbial processing cycle in the chamber. The concentration of the agent vapor in the load-simulating device during the cycle is sensed, and an electronic parameter value is generated. The method controls vapor concentration, chamber temperature, and/or cycle duration in real-time in response to the sensed parameter value.

In another aspect, the present invention provides a method of monitoring an anti-microbial parameter in a decontamination system by selecting a resistance barrier having certain characteristics, disposing the barrier between a sensor and an anti-microbial agent, and monitoring a control signal provided by the sensor indicating a parameter associated with the anti-microbial agent.

The present invention may be used with a wide array of anti-microbial processing systems including, but not limited to, steam, ethylene oxide gas, liquid and vaporized hydrogen peroxide, liquid and vaporized formaldehyde, liquid and vaporized peroxy compounds, ozone, ionized gases, plasmas, chlorine-based agents, and combinations thereof.

One advantage of the present invention is that it enables an anti-microbial process such as a sterilization or disinfection cycle to be monitored and controlled in real-time.

Another advantage of the present invention is that it enables a determination to be made while an anti-microbial process, such as a sterilization or disinfection cycle, is in progress whether the necessary conditions for the process have been achieved.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIGS. 5A, 5B and 5C schematically illustrate another embodiment of a load-simulating device of the invention.

FIG. 6 illustrates an example of the pre-exposure phase of a steam sterilization cycle which may be employed in the invention.

FIG. 8 illustrates an example of a timing cycle which may be employed in the invention.

DESCRIPTION OF THE PREFERRED EMBODIMENTS

Figure 1A:
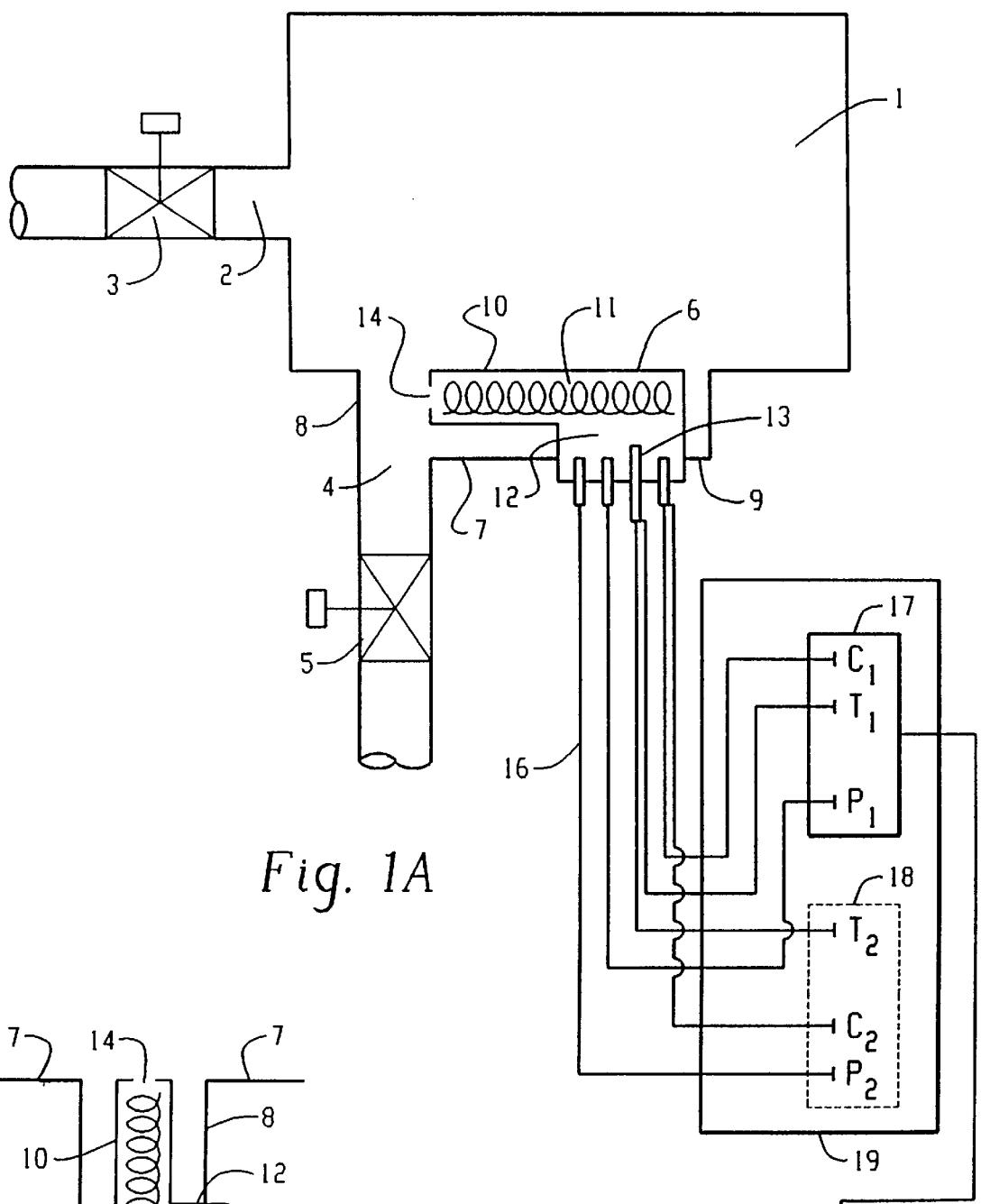
FIG. 1A is a schematic illustration of the present invention, including a load-simulating device connected to a sterilization chamber and sensor probes integrated into the sterilizer control system and a parametric release monitoring system.

The present invention relates to an apparatus and method for anti-microbial processing. The term "anti-microbial processing" includes, but is not limited to, various treatment techniques and methods for reducing or eliminating microorganisms or their ability to reproduce, such as for example decontamination, sterilization, disinfection, sanitization, and combinations of these techniques. The term "decontamination apparatus" is used herein to refer to an apparatus or system for performing any of these anti-microbial processing techniques.

In particular, the present invention is concerned with the real-time control of anti-microbial processing parameters within a load-simulation device that simulates the same conditions as those within an acceptable standard challenge load to be decontaminated. Integration of such a load-simulating device into a decontamination apparatus chamber and parameter sensing system allows real-time monitoring and transmission of cycle parameter values from the load-simulating device to the control system. If the parameter values fall outside the range of acceptable values, the control system directs the operation of control means, such as heaters, valves, pumps, timers, etc. in real time to bring the parameter values into an acceptable range within the load-simulating device. Thus, optimum and efficacious anti-microbial processing conditions can be achieved and maintained within the load (as measured by the conditions sensed within the load-simulating device) resulting in a significant reduction in the number of unsuccessful cycles. Moreover, when acceptable anti-microbial processing parameters are shown to have been met, the processed load is automatically released for use immediately upon completion of the cycle. Thus, the need for biological indicators and chemical integrators is eliminated.

The invention may be used with any anti-microbial process in which a successful outcome depends on achieving and maintaining controllable decontamination parameters for a given time. Such anti-microbial processes include, but are not limited to, decontamination, sterilization, disinfection, or sanitization with steam, ethylene oxide gas, liquid and vaporized hydrogen peroxide, liquid and vaporized formaldehyde, liquid and vaporized peroxy compounds, ozone, ionized gases, plasmas, and combinations thereof. Other suitable agents include chlorine-based agents such as for example, chlorine gas, hypochlorites, chlorine dioxide, certain chloramines, chlorine trifluoride, chlorine pentafluoride, and combinations of these and other agents. These agents may, in most instances, be in gas or liquid form.

The load-simulating device is integrated into the decontamination parameter sensing and control system and employs one or more resistance barriers resistant to penetration of the anti-microbial agent, such as in the form of a tortuous path, similar to the barrier encountered by a sterilant penetrating a load of wrapped goods or goods in a sealed pouch. The acceptable standard challenge load simulated by the load-simulating device reflects a "worst-case" load to be processed. Therefore, each type of resistance barrier in the load-simulating device is specifically designed for the particular anti-microbial agent to be employed in order to accurately simulate load conditions, or worst-case conditions, using the specified agent. For example, for sterilants such as hydrogen peroxide vapor, a sufficient resistance barrier may comprise a tortuous path for entrance of the sterilant into the device. For other sterilants, such as ethylene oxide gas, the resistance barrier may additionally or alternatively comprise another tortuous path within the interior of the device, such as a packed material or a baffle or series of baffles. The resistance barrier may be purely a physical barrier and/or may also comprise a physical or chemical material which is slightly absorptive of the agent. Suitable resistance barrier materials may include, but are not limited to, cellulosic materials for steam and/or ethylene oxide sterilants, a wide array of tetrafluorethylene fluorocarbon polymers generally known as TEFLON™, silicon, polypropylene and polycarbonate materials for ethylene oxide and/or hydrogen peroxide sterilants, and combinations thereof. Effective resistance barrier materials for other sterilants, such as formaldehyde, ozone, or ionized gases and plasmas, are known to persons skilled in the art of sterilization.

Figure 1B:
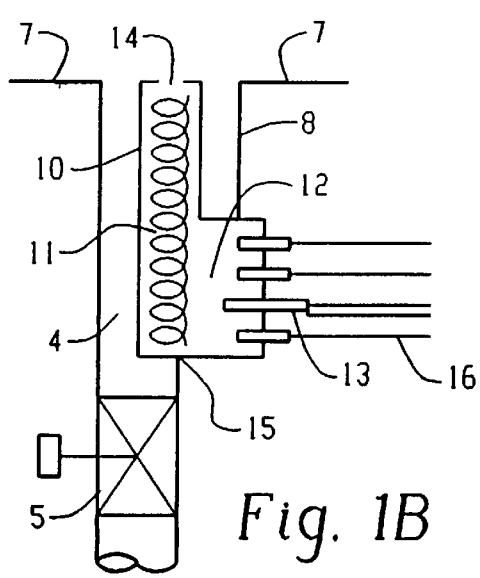
FIG. 1B is a schematic illustration of a load-simulating device positioned within a sterilizer drain line.

Turning now to the figures, it is to be understood that although the preferred embodiments are described in conjunction with a sterilizer and sterilization cycle, the present invention is not limited to such. As illustrated in FIGS. 1A and 1B, the system includes a sterilization chamber 1 having a sterilant inlet 2 and sterilant inlet valve 3 and a chamber drain line or exhaust outlet 4 and chamber outlet valve 5. A load-simulating device 6 is located within the chamber 1 and is removably connected to a chamber wall 7 or chamber drain wall 8 as described herein below. If connected to a chamber wall 7, the load-simulating device 6 is preferably located in a recessed portion 9 of the chamber wall 7, such that the load-simulating device 6 does not interfere with loading and unloading of goods in the chamber 1. When the device 6 is employed in a steam sterilization chamber, it is more preferable to locate the device 6 close to or within the drain line 4 in order to detect more readily the presence of unwanted air that will tend to settle there, as known in the art, and allow for correction of the problem, as described herein below.

Figure 2:
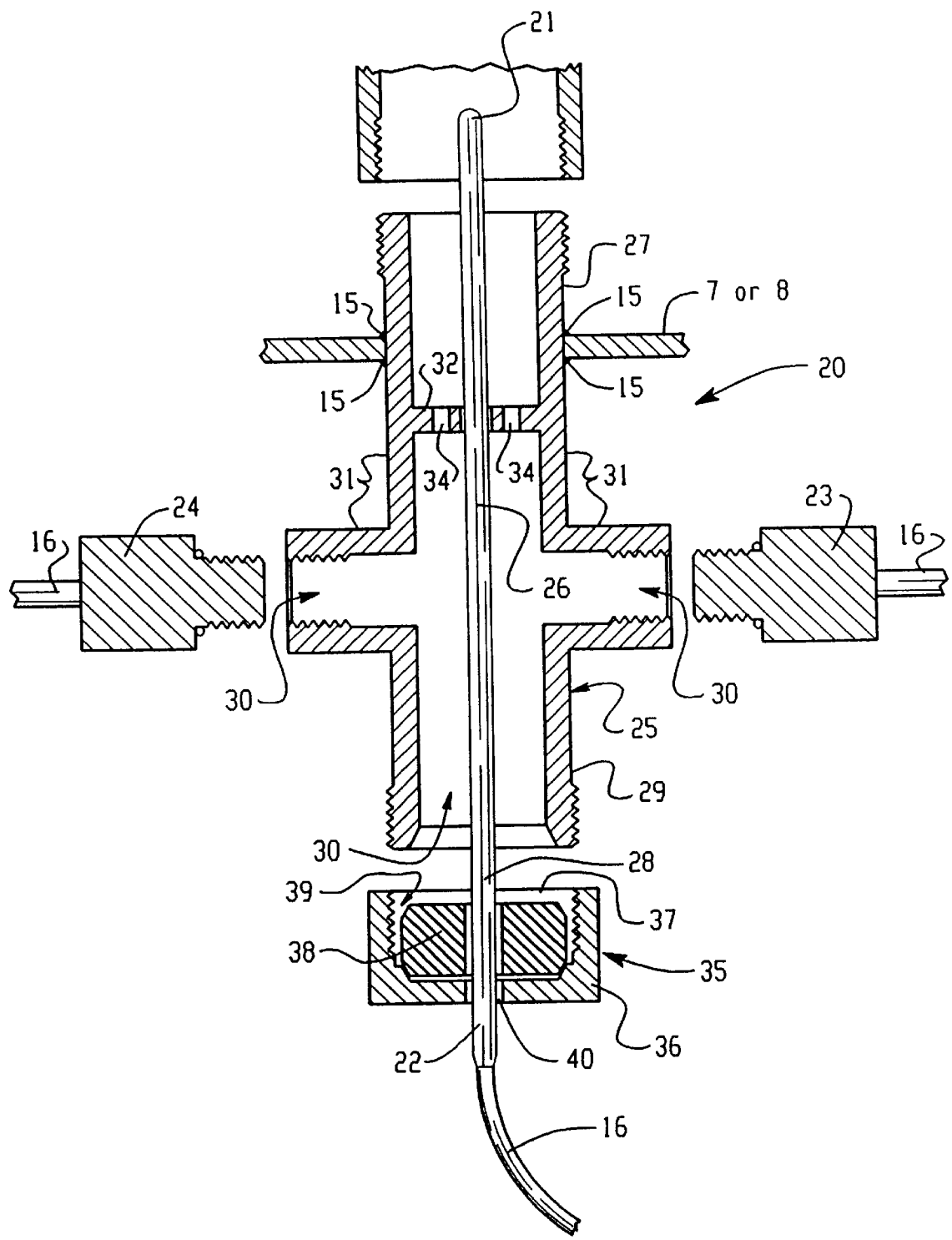
FIG. 2 illustrates an embodiment of a sensor fitting in accordance with the invention.
Figure 3A:
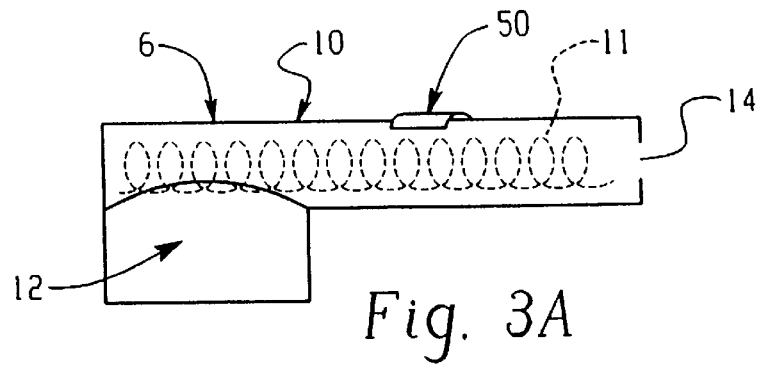
FIGS. 3A, 3B and 3C are schematic illustrations of the load-simulating device of the invention.
Figure 3B:
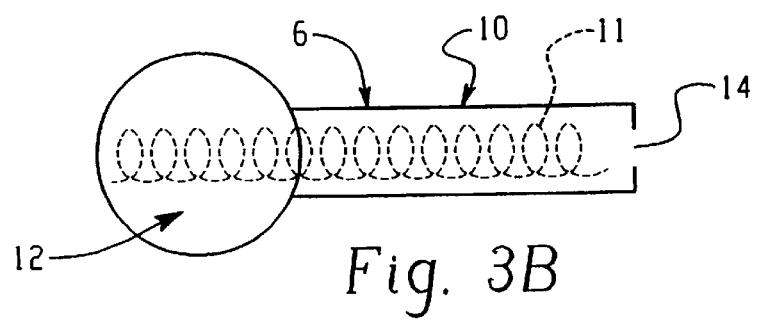

In the embodiment illustrated in FIGS. 1A and 1B, and shown schematically in FIGS. 3A and 3B, the load-simulating device 6 comprises a housing 10 for a resistance barrier 11 to penetration of a sterilant and a receiving area 12 for sterilant that successfully penetrates the resistance barrier 11. At least one sensor probe 13 is positioned in the receiving area 12 of the load-simulating device 6 for real-time sensing and monitoring of at least one sterilization parameter value during a sterilization cycle. A connection flange or a weld fillet 15 (more clearly shown in FIG. 2) connects the device 6 to the sterilization chamber wall 7 or drain line wall 8 at or near the location of the sensor probe 13. An optional use indicator 50 is preferably positioned on a surface of the load-simulating device 6 in contact with the chamber environment. The use indicator 50 serves only to indicate, preferably by a visible color change, that the load-simulating device 6 has been exposed to a sterilant. The use indicator 50 is not intended to serve as a chemical integrator.

In the embodiment illustrated in FIGS. 1A and 1B, the housing 10 of the device 6 is constructed with a small opening 14 at one end, to allow a liquid, gas or vapor sterilant to enter into the interior of the device 6. The illustrated opening in the housing is used in conjunction with the interior resistance barrier 11 that provides a tortuous path for the sterilant. However, the sterilant may alternatively enter the device by another route, preferably one that provides a tortuous path/resistance barrier, such as through a seam in the housing, or penetration by wetting through material comprising the housing wall. In this case, the additional resistance barrier 11 in the interior of the device may also be included or be optional. Therefore, the device is intended to provide one or more resistance barriers/tortuous paths, depending on the characteristics of the sterilant employed.

Regardless of the route of sterilant entry, the load-simulating device 6 itself, as defined by the housing 10, is preferably shaped to simulate a dead-ended lumen, known to be difficult to sterilize because of the known difficulty of sterilant penetration into lumens in general. Therefore, in a preferred embodiment, the device 6 itself, by virtue of simulating a dead-ended lumen, comprises a resistance barrier to penetration of the sterilant.

During a sterilization cycle, the liquid, gas or vapor sterilant in the sterilization chamber 1 enters the load-simulating device 6 and is constrained to follow a prescribed path. The sterilant passes through the optional resistance barrier 11 and sterilant that penetrates the barrier 11 reaches the receiving area 12 where it comes into contact with the sensor probe 13. Therefore, there is a fluid connection between the sterilization chamber 1 and the sensor probe 13.

The sensor probe 13 may be present as a single probe or a plurality of probes or sensing elements. Parameters which may be sensed by the sensor probe or probes 13 include, but are not limited to, temperature, pressure, concentration of sterilant, relative humidity and multiples and combinations of these. For example, a set of sensor probes may contain two or more pressure sensors P1, P2 and two or more temperature sensors T1, T2 and two or more chemical sterilant concentration sensors C1, C2; and each parameter may be sensed by two or more separate sensing probes or by a single probe housing two or more sensing elements. As described herein below, multiple probes, preferably dual probes, for sensing a particular parameter are employed to comply with ISO and/or CEN standards requiring a separate set of sensing probes for parameter control and for parametric release of the load. Multiple probes, for example, an array of concentration-sensing elements, may be necessary in order to determine the concentration of certain chemical sterilants, such as multicomponent sterilants.

A transmitting means 16 is connected to each sensor probe or sensing element 13 for transmitting a sensed parameter value from the sensor probe 13 to a receiving means 19, such as the sterilizer control system 17 or a parametric release monitoring system 18. The transmitting means 16 may comprise any means that is capable of transmitting the sensor data to the receiving means 19 including, but not limited to, electrical connection of the sensor probe 13 to the receiving means 19 and electronic or radio frequency transmission of the sensor data to the receiving means 19.

The sterilizer control system 17 may be any system including, but not limited to, a microprocessor or a logic circuit that is programmed to receive the sensed parameter value and also to control the value of the parameter in real time during the sterilization cycle by governing a plurality of parameter control means 100 which operate valves, pumps, timers, heaters, etc. The sterilizer control system 17 is also programmed to store a predetermined reference sterilization parameter range and to compare the received sensed parameter value to the reference parameter range. If the sensed parameter value falls within the reference parameter range, acceptable sterilization conditions are indicated, and the cycle continues. If the sensed parameter value falls outside of the reference parameter range, the sterilizer control system 17 is programmed to signal the parameter control means 100 to operate until the value of the sensed parameter falls within the reference parameter range. Thus, if the sensed temperature reading in the load-simulating device 6 is below an acceptable limit, the sterilizer control system 17 signals the parameter control means 100 to operate a chamber heating means (not shown) until the temperature reading of the temperature-sensing probe 13 in the load-simulating device falls within the range that is acceptable for sterilization. If a sensed sterilant concentration in the load-simulating device 6 is below the acceptable limit, the sterilizer control system 17 signals the parameter control means 100 to control the operation of a sterilant injector (not shown) to increase the concentration of sterilant injected into the chamber 1, until the concentration of sterilant sensed by the concentration-sensing probe 13 is at an acceptable value, or within a range of acceptable values. In each of these examples, the sterilizer control system 17 also signals a timer (not shown) to be reset to compensate for the time during which the sterilization cycle experienced unacceptable conditions. In many sterilization cycles, critical parameters are interdependent. For example, in a vapor hydrogen peroxide sterilization system, the concentration of the vapor that is allowable (i.e. does not exceed the dew point concentration) in the load at any given time is dependent on the temperature, pressure, and/or relative humidity in the load at that time. Therefore, in systems such as these, the sterilizer control system is programmed to monitor more than one parameter and analyze the data to determine whether or not the environmental conditions are within the acceptable range of values.

In each embodiment of the invention, a redundant set or sets of temperature, pressure or other sensors 13, such as relative humidity or chemical sterilant concentration sensors may be incorporated. For example, in a preferred embodiment as illustrated in FIG. 1A, one set of sensor probes T2, P2, C2 is used only as a parametric release monitoring system 18, for monitoring sterilization parameters to determine if acceptable sterilization conditions in the load-simulating device 6 have been achieved and the load may be released as sterilized. Another set of sensors probes T1, P1, C1 in the load-simulating device 6 transmits readings of temperature, pressure or other parameter levels to the sterilizer control system 17 for controlling the process parameters by the parameter control means 100. In this embodiment, the release monitoring sensors T2, P2, C2 are preferably connected to a user interface (display and/or printout) circuit (not shown) which is separate from the circuit (not shown) that connects the sterilizer control system 17 and the sensors T1, P1, C1 that provide data for process control. This feature addresses the concern outlined in current CEN and ISO standards for the need to keep the parametric release system independent of the system that controls the sterilizer cycle. The independent release monitoring sensors act as a back-up and redundant system to the sensors integrated into the sterilizer control system. Thus, erroneous release of a load that is not sterilized because sensors used for control purposes falsely indicate (e.g. due to being out of calibration or subject to a component or electrical failure) that sterilization conditions are being achieved, is virtually prevented.

FIG. 2 illustrates an embodiment of one possible sensor fitting 20 for use in the present invention, for containing at least one 22, and preferably a plurality of sensor probes 22, 23, 24), and for attaching the sensor probe or probes to the load-simulating device 6, and to the chamber wall 7 or drain wall 8. It is envisioned that any sensor fitting which is capable of accommodating the sensor probes and load-simulating device and accomplishing the objectives of the invention, may be alternatively used in the practice of the invention. In the illustrated embodiment, at least one each of a temperature sensor probe 22, a pressure sensor probe 23 and a chemical sterilant concentration sensor probe 24 are used in the practice of the invention. However, these probes are meant to be representative only, and are interchangeable with probes measuring other parameters, such as relative humidity. They may also represent a plurality of one or more types of probes, such as a plurality of concentration-sensing probes for different components of a multicomponent chemical sterilant, or a plurality of temperature or pressure sensing probes.

As illustrated in FIG. 2, this embodiment of the sensor fitting 20 comprises a housing 25 having an outer wall and an interior wall which defines a hollow interior having a first end 27 and a second end 29 and side walls 31. The first end 27 of the sensor fitting 20 is shaped to protrude into the interior of the chamber 1 through a complementary opening in the chamber wall 7 or chamber drain wall 8. The outer wall of the housing 25 is secured to the chamber wall 7 or drain wall 8 by means of a connection flange or a weld fillet 15 that provides a seal between the sensor fitting 20 and the chamber wall 7 or drain wall 8. The second end 29 of the sensor fitting 20 extends exteriorly from the chamber wall 7 or drain wall 8. The first end 27 and second end 29 and the side walls 31 of the sensor fitting 20 comprise openings 30 for receiving a sensor probe or plurality of sensor probes (see below). As illustrated in this embodiment, a temperature sensor probe 22 extends through the hollow interior of the length of the sensor fitting 20 and comprises a tip portion 21 which protrudes beyond the open first end 27 of the sensor fitting 20, a middle portion 26 contained within the hollow interior of the sensor fitting 20, and a base portion 28 which extends beyond the open second end of the sensor fitting 20. The position of the temperature probe 22 within the hollow sensor fitting 20 may be optionally stabilized by means of a support flange 32, connected to an interior wall of the housing 25, containing a plurality of openings 34 sufficient to ensure that a fluid environment is maintained throughout the hollow interior of the sensor fitting 20.

As described herein above, the housing 25 of the sensor fitting 20 comprises an opening or a plurality of other openings 30 for receiving other sensor probes. The probes illustrated in FIG. 2 include, but are not limited to, a pressure sensing probe 23 and/or a chemical sterilant concentration sensing probe 24. Each of the sensor probes 23, 24) is in fluid connection with the hollow interior of the sensor fitting 20 and is engaged, preferably threadably engaged, to the housing 25 to form a seal between the sensor probe 23, 24 and the sensor fitting 20. Each of the sensor probes 22, 23, 24 terminates in a separate transmission means 16, extending from each probe and external to the sensor fitting 20 for transmitting sensed data to the receiving means 19.

The base portion 28 of the temperature probe 22, including the transmitting means 16, further extends through a compression fitting 35 comprising a housing 36 defining an anterior opening 37 containing a flexible ring member 38, preferably a ferrule, that encircles the base portion 28 of the probe 22 and a space 39 surrounding the ring member 38, and a posterior opening 40 for affording the passage of the base portion 28 of the temperature probe 22 therethrough, the transmission means 16 extending exteriorly from a posterior opening 40. The compression fitting 35 is removably engagable to the second end 29 of the sensor fitting 20. A pressure-tight seal between the compression fitting 35 and the sensor fitting 20 is achieved when the second end 29 of the sensor fitting 20 threadably engages the anterior opening 37 of the compression fitting 35, occupies the space 39 between the housing 36 and the ring member 38 and, thereby, sealably compresses the ring member 38 around the temperature probe 22.

As described herein above, the first end 27 of the sensor fitting 20 is shaped to protrude into the interior of the chamber 1 through a complementary opening in the chamber wall 7 or chamber drain wall 8. The first end 27 of the sensor fitting 20 is also removably and sealably connectable, preferably threadably connectable, to the load-simulating device 6 within the chamber 1. As described herein above, the tip portion 21 of the temperature probe 22 extends beyond the first end 27 of the sensor fitting 20. In a preferred embodiment, when the sensor fitting 20 is connected to the load-simulating device 6, the tip portion 21 of the temperature probe 22 extends into the receiving area 12 of the load-simulating device 6 but does not contact or extend into the resistance barrier 11.

When a sensor fitting 20 such as that described in FIG. 2 is employed, there are a number of possible embodiments for the inter-connection of the sensor probes 13, the load-simulating device 6, and the transmitting means 16. For example, in one embodiment schematically illustrated in FIG. 1A, the sensor probes 13 including the transmission means 16 connecting the probes 13 to the sterilizer control system 17 are preconnected and premounted via the sensor fitting 20 of FIG. 2 to the chamber wall 7 or drain line 8. Thus, the load-simulating device 6 is removably connected to the premounted sensor fitting 20 inside the chamber wall 7 or drain wall 8 at the location of the probes 13 in the manner illustrated in the embodiment of FIG. 2. In this embodiment, the load-simulating device may be, and preferably is, disposable. Alternatively the device may be reusable if, for example, it is recharged or dried out (in the case of a sterilization cycle involving moisture). The sensor probes may be permanently or temporarily mounted to the chamber, as desired.

Figure 3C:
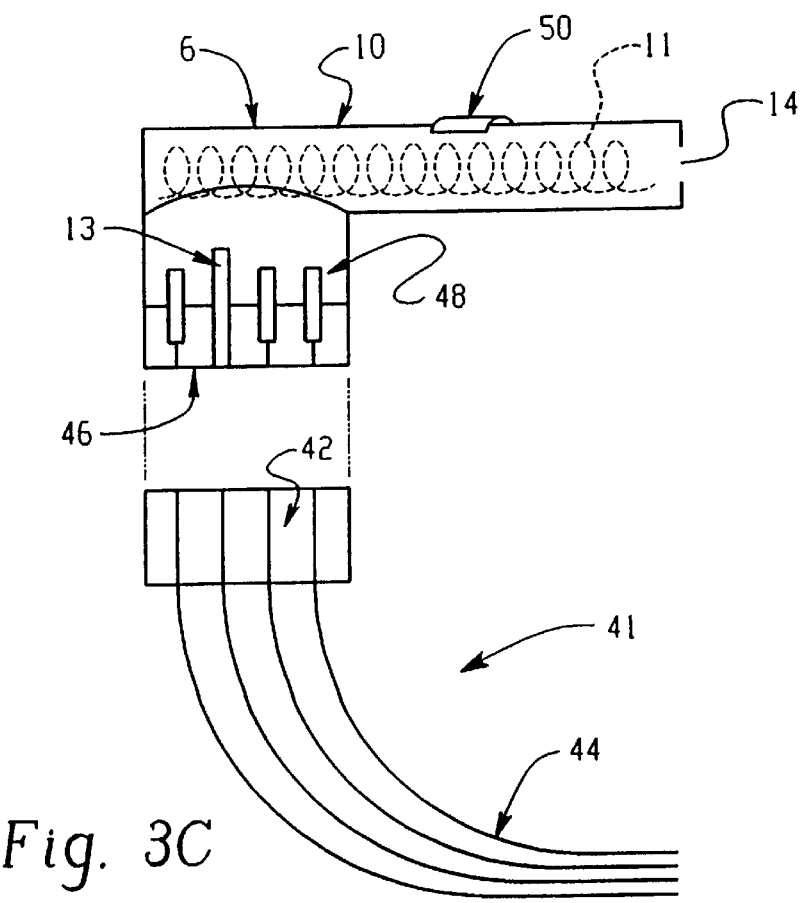

In another embodiment, schematically illustrated in FIG. 3C, sensor probes 48 are removably connectable to the load-simulating device as illustrated in FIG. 2 and described herein above. However, in this embodiment, a sensor connector 41, which may extend into the interior of the chamber, has a electrical connector portion 42 connected to the chamber wall 7 or drain line 8, and a signal transmission means portion 44 connectable to a signal receiver (not shown). The sensor probes 48 terminate in one or more complimentary electrical interface(s). Thus, in this embodiment, the sensor probes 48 may be preconnected to a load-simulating device and then interfaced to the sterilizer control via an electrical connection inside the chamber. In this embodiment, the sensor probes may also be reusable and/or disposable.

FIGS. 4 and 5 illustrate embodiments of a load-simulating device which may be employed in the present invention. The precise nature of the load-simulating device to be used for a given sterilization cycle depends on the nature of the sterilant and the sterilization parameters to be monitored. For example, a load-simulating device for a steam sterilization cycle, a hydrogen peroxide vapor sterilization cycle and an ethylene oxide sterilization cycle, etc. may be different from each other, because of different critical sterilization parameters and sterilant properties. Thus, for steam, the resistance barrier in the load-simulating device preferably comprises a barrier material, such as a cellulosic, that absorbs heat, and the sensors within the device preferably monitor and provide for control of both temperature and pressure within the device. For an ethylene oxide sterilant, a tortuous path for penetration of the sterilant into and through the device preferably comprises a physical barrier to the flow of the gas. The materials selected for the barrier are determined by the solubility and diffusion rate of the ethylene oxide in the material and the thickness of the barrier. For example, ethylene oxide has a higher diffusion rate through silicon than through polyethylene, so polyethylene is preferable to silicon as a barrier material. The sensor probes employed for an ethylene oxide cycle preferably monitor and provide for control of temperature, pressure, relative humidity and concentration of the sterilant within the load-simulating device. A preferable load-simulating device for hydrogen peroxide liquid or vapor sterilization includes a dead-ended device and a resistance barrier comprising a physical restriction of the flow of the sterilant (e.g. through a restricted orifice or orifices) and/or requiring changes in direction of flow (e.g. around baffles). The preferred materials of construction of the resistance barrier comprise those which inhibit gas penetration and do not substantially absorb the sterilant. Thus, for hydrogen peroxide sterilization, polyethylene, polypropylene, TEFLON™, silicon, and polycarbonate are preferred materials. The sensor probes employed for a vapor hydrogen peroxide cycle preferably monitor and provide for control of temperature, pressure, relative humidity and concentration of the sterilant within the load-simulating device.

The preferred load-simulating devices generally include a housing defining one or more resistance barriers to the passage of a sterilant and a receiving area where sterilant which has penetrated the resistance barrier(s) comes into contact with one or more sensor probes. As described herein above, one of the resistance barriers may be a dead-ended lumen defined by the housing.

Figure 4A:
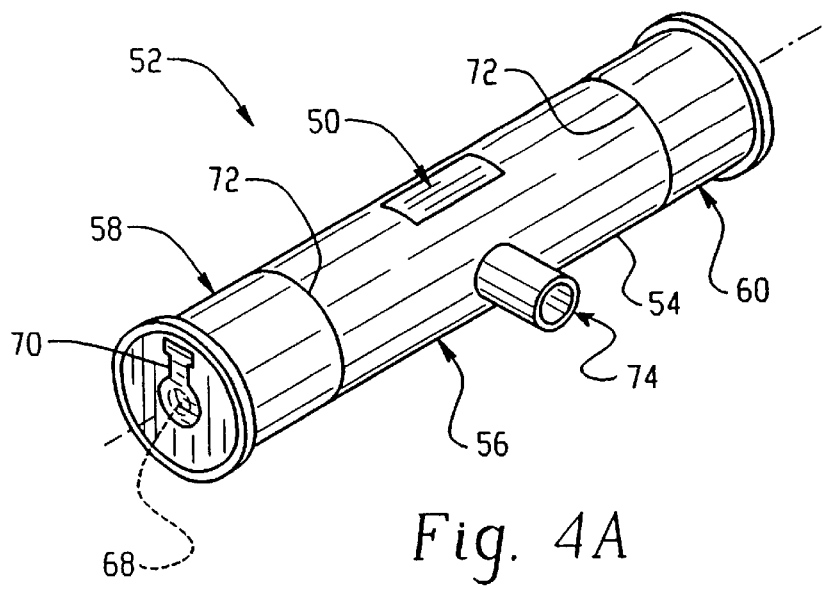
FIGS. 4A and 4B illustrate an embodiment of a load-simulating device of the invention in a closed configuration and an exploded view, respectively.
Figure 4B:
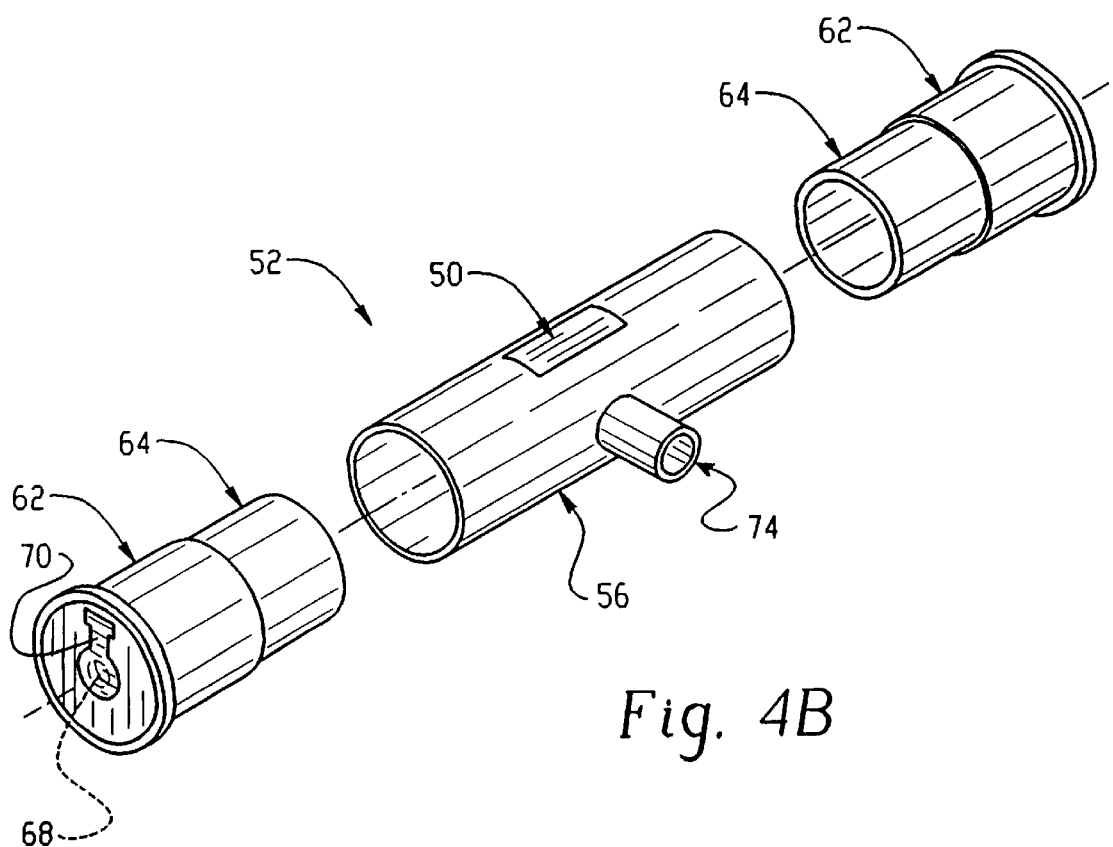

The load-simulating device shown in FIG. 4A in a closed configuration and in FIG. 4B in an exploded view is illustrative of a housing comprising a tortuous path for entry of a sterilant into the interior of the device. A typical exterior housing for use in a steam or ethylene oxide sterilization cycle is disclosed in commonly owned U.S. Pat. Nos. 4,839,291 and 4,914,034, the disclosures of which pertaining to tortuous paths through the housing of the device are hereby incorporated by reference. In brief, the housing 54 of a canister 52 comprises a central tubular portion 56, a first tubular end portion 58 and a second tubular end portion 60. The central tubular portion 56 has two open ends. Each of the tubular end portions 58, 60) includes an outer member 62 having a closed end, and an inner member 64 having an open end. The outer member 62 of tubular end portion 58 further has a hole or opening 68 in its closed end that is covered with an adhesive backed tab 70. The tab 70 permits the optional opening or closure of hole 68. The inner members 64 of each of the end portions 58, 60 telescope into the central tubular portion 56 of the housing 54 allowing each of the outer members 62 to abut the central tubular portion 56 and form seam or gap 72 between the central tubular portion and the outer members 62 of the tubular end portions 58,60. The seam or gap 72 forms a tortuous path for entry of the sterilant into the interior of the canister 52. Further, the seam or gap 72 may optionally be covered by a sterilant-permeable layer (not shown), such as medical grade paper, to form a further tortuous path for entry of the sterilant into the interior. Another tortuous path for entry of the sterilant is defined by the close tolerance between the telescoping surfaces of the central tubular portion 56 and inner members 64 of the end portions 58, 60 of the housing 54. As practiced in the present invention and described herein previously, the device may optionally contain a further resistance barrier (not shown) to sterilant passage, such as a packed material or a baffle or series of baffles, within the interior of the device. Preferably, such an internal resistance barrier is employed when the sterilant enters the canister through opening 68 when tab 70 is removed. Other examples of resistance barriers, include but are not limited to, perforated members.

The central tubular portion 56 of the canister 52 illustrated in FIG. 4 includes a connection fitting 74 that is removably connectable to a sensor fitting, as illustrated in FIG. 2. The device optionally has a use indicator 50 positioned on an exterior surface.

FIGS. 5A, 5B and 5C illustrate another embodiment of a load-simulating device which incorporates a tortuous path in the interior of the device. A typical device may include a tortuous path as described for a steam sterilization cycle disclosed in commonly owned U.S. Pat. No. 4,594,223, the disclosure of which pertaining to tortuous paths is hereby incorporated by reference. However, the tortuous path may be different from the disclosed device (e.g. baffles, etc.) depending on the sterilant employed, as described herein above. Briefly, the device 80 comprises a resistance barrier 82 within a canister housing 84 and a use indicator 50 on the exterior of the canister. One end of the housing 84 is in fluid communication with the chamber environment and has an opening 86 for the passage of a sterilant into and through the length of the device. The receiving area 88 for sterilant fluidly penetrating the resistance barrier 82 has a connection fitting 90 at the opposite end for removable attachment to a sensor fitting as shown in FIG. 2. As shown in cross-section in FIG. 5C, the receiving area 88 is constricted to prevent resistance barrier material from entering the receiving area. As more fully described in U.S. Pat. No. 4,594,223, if steam sterilization is employed the constriction also serves as a collection area for any unwanted air mixed with the steam, the air being in fluid contact with the sensors, to allow control of the cycle for correction of the problem or aborting of the cycle.

The materials from which the housing of the load-simulating device and/or any internal resistance barrier are manufactured may be different from each other and are selected to be compatible with the anti-microbial agent or sterilant employed. The housing material may be slightly absorptive of the agent or sterilant, but may not be so absorptive as to affect the concentration level of agent or sterilant in the chamber in the area surrounding the device or to result in high levels of residual agent or sterilant which may be difficult to remove at the completion of the cycle. Suitable, and preferred, housing and/or resistance barrier materials may include, but are not limited to, cellulosic materials for steam and/or ethylene oxide sterilants; TEFLON™, silicon, polypropylene and polycarbonate materials for ethylene oxide and hydrogen peroxide sterilants; and combinations thereof.

Figure 7:
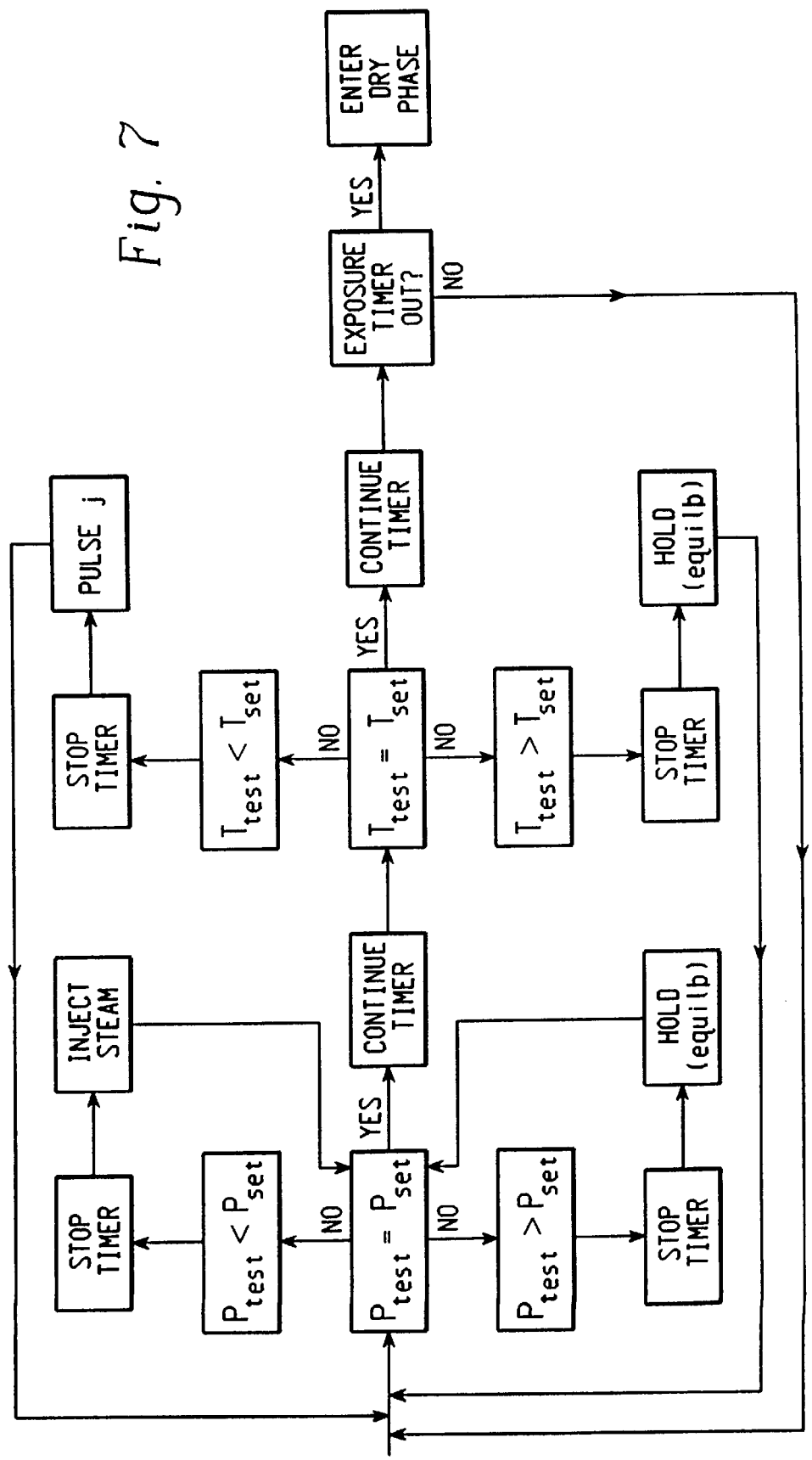
FIG. 7 illustrates an example of the exposure phase of a steam sterilization cycle which may be employed in the invention.

FIGS. 6, 7, and 8, illustrate the method of the invention in a typical steam sterilization cycle employing the real-time monitoring and control of cycle parameters within the load-simulating device and parametric release of the load for use when the parameters are met. Again, it is to be understood that although the preferred embodiment methods and techniques are described in terms of a sterilization process, the present invention is not limited to such. And, although a steam sterilization cycle is illustrated, the method of the invention can be modified by one skilled in the art to accommodate any sterilant, such as ethylene oxide, hydrogen peroxide, formaldehyde, ozone, peroxy compounds, chlorine-based agents, and the like. For a steam sterilization cycle, the parameters of temperature, pressure and time are preferably monitored. For an ethylene oxide cycle, the parameters of temperature, pressure, relative humidity, time, and the concentration of ethylene oxide are preferably monitored. For a chemical sterilant, such as liquid or vaporized formaldehyde or liquid or vaporized hydrogen peroxide, the parameters of temperature, pressure, relative humidity, time, and the concentration of the sterilant are preferably monitored.

As illustrated in FIG. 6, the method of the invention begins with a pre-exposure phase pulse number "i" 101 which, for a pre-vacuum type sterilizer is typically a vacuum pull and steam charge, and for an gravity type sterilizer is typically a steam flush with an open drain line. Following "Pulse i", the pressure in the load-simulating device (test device) is sensed by the pressure probe. If, for example due to air in the device, the sensed pressure ($P_{test} \pm Z$ psia) does not fall within an acceptable predetermined setpoint pressure ($P_{set} \pm Z$ psia) range, the sterilizer control system signals the parameter control means 100 to produce another pulse i+1 103. Extra pulses continue only until the pressure sensor indicates that $P_{test} = P_{set}$ 102. The number of extra pulses is limited (to six or less, in the illustration) 104 or the cycle is aborted 105 in order to prevent an infinite cycle which could occur, for example, in the event of a chamber air leak. When $P_{test} = P_{set}$ 102, a pass situation is indicated, and the temperature is sensed by the temperature probe. If the sensed temperature ($T_{test} \pm Y°$ C.) does not fall within an acceptable predetermined setpoint temperature ($T_{set} \pm Y°$ C.) range, for example due to the presence of air in the device, the sterilizer control system signals the parameter control means 100 to produce another pulse. When $T_{test} = T_{set}$ 106, a pass situation is indicated and the cycle enters the exposure phase 107 illustrated in FIG. 7 and starts the exposure timer 108. The same principles of pass/fail apply to the sensed pressure and temperature in the load-simulating device during this exposure phase. Whenever the sensed pressures or temperatures are not acceptable, the exposure timer is stopped 120 for the time required to bring the parameters into the acceptable range, as illustrated in FIG. 8. If the elapsed time ($T_{elapse}$) 121 exceeds a certain set point (900 seconds, in the example) 122, the cycle is aborted 123, in order to avoid an infinite cycle.

Throughout the cycle, the monitoring sensors in the load-simulating device transmit data to a receiving means comprising a parametric release sensing system. When the data indicate that the critical parameters of the cycle have been achieved in the load-simulating device, the parametric release system presumes the load has been sterilized. The parametric release monitoring system thus allows release of the load for use when the monitored sterilization parameter levels indicate sterilization cycle efficacy within the load-simulating device.

While the invention has been described herein with reference to the preferred embodiments, it is to be understood that it is not intended to limit the invention to the specific forms disclosed. On the contrary, it is intended to cover all modifications and alternative forms falling within the spirit and scope of the invention.

We claim:

1. A system for monitoring and controlling an anti-microbial processing cycle, the system comprising:

a challenge load-simulating device, said device comprising a resistance barrier that is resistant to passage of an anti-microbial agent and a receiving area for the agent that passes said resistance barrier;

a first sensor probe positioned in said receiving area for real-time sensing of an anti-microbial processing parameter value during an anti-microbial processing cycle, said anti-microbial processing parameter being concentration of said anti-microbial agent;

a control system for controlling the value of said parameter in real time during said cycle; and a first transmitting circuit in communication with said first sensor probe for transmitting the sensed parameter value from said first sensor probe to said control system.

2. The system of claim 1, wherein said control system is programmed to store a predetermined reference parameter range.

3. The system of claim 2, wherein said control system is programmed to receive said sensed parameter value and compare said sensed parameter value to said stored reference parameter range.

4. The system of claim 3, wherein said control system is programmed to indicate acceptable anti-microbial processing conditions when said sensed parameter value is within said reference parameter range.

5. The system of claim 4, wherein said control system is programmed to change the value of said parameter when said sensed parameter value is outside said reference parameter range.

6. The system of claim 1, further comprising:

a second sensor probe positioned in said receiving area of said challenge load-simulating device for real-time sensing therein of an anti-microbial processing parameter value during said anti-microbial processing cycle; and a second transmitting circuit in communication with said second sensor probe for transmitting the sensed parameter value from said second sensor probe to said control system.

7. The system of claim 1, wherein said anti-microbial processing parameter is selected from the group consisting of temperature, pressure, relative humidity, anti-microbial agent concentration, time, and multiples and combinations thereof.

8. The system of claim 1, wherein said anti-microbial agent is selected from the group consisting of steam, ethylene oxide gas, liquid hydrogen peroxide, vaporized hydrogen peroxide, liquid formaldehyde, vaporized formaldehyde, liquid peroxy compounds, vaporized peroxy compounds, ozone, ionized gases, plasmas, chlorine-based agents, and combinations thereof.

9. A challenge load-simulating device comprising:
 a semi-permeable barrier characterized by being resistant to penetration of an anti-microbial agent and selected from the group consisting of a tortuous path for entrance of said anti-microbial agent into said device, a tortuous path for said anti-microbial agent within said device, and multiples and combinations thereof;
 a receiving area defined within said device for receiving the anti-microbial agent that penetrates said resistance barrier;
 a sensor probe disposed in said receiving area of said challenge load-simulating device for real-time sensing therein of an anti-microbial processing parameter value during an anti-microbial processing cycle and transmitting in real-time said parameter value to a control or monitoring system for real-time control or monitoring of said anti-microbial processing parameter during said anti-microbial processing cycle; and
 a control system for controlling the value of said anti-microbial processing parameter in real-time in response to sensing by said sensor probe of said parameter during said anti-microbial processing cycle.

10. The device of claim 9, wherein said semipermeable barrier comprises a material selected from the group consisting of cellulosics, tetrafluoroethylene fluorocarbon polymers, silicon, polypropylene, polyethylene, polycarbonate, and combinations thereof.

11. The device of claim 9, wherein said anti-microbial agent is selected from the group consisting essentially of steam, ethylene oxide gas, liquid hydrogen peroxide, vaporized hydrogen peroxide, liquid formaldehyde, vaporized formaldehyde, liquid peroxy compounds, vaporized peroxy compounds, ozone, ionized gases, plasmas, chlorine-based agents, and combinations thereof.

12. A method for monitoring and controlling a parameter value in a simulated load during an anti-microbial process performed in a decontamination apparatus having a control system, said method comprising the steps of:
 (a) positioning a challenge load-simulating device in said decontamination apparatus, said device comprising a resistance barrier resistant to penetration of an anti-microbial agent and a receiving area for said anti-microbial agent that penetrates said resistance barrier, said anti-microbial agent being a chlorine-based agent and selected from the group consisting of chlorine gas, hypochlorites, chlorine dioxide, chloramines, chlorine trifluoride, chlorine pentafluoride, and combinations thereof;
 (b) sealably fitting a first sensor probe within said device, such that said first sensor probe is positioned in said receiving area for real-time sensing therein of a parameter value during the anti-microbial process, said first sensor probe comprising a transmitting means for transmitting the sensed parameter value from said first sensor probe to said control system;
 (c) exposing said load-simulating device to said chlorine-based anti-microbial agent during said anti-microbial process;
 (d) sensing in real-time said parameter value within said receiving area of said device during said process;
 (e) transmitting in real-time the sensed parameter value in said load-simulating device from said first sensor probe to said control system; and
 (f) controlling the value of said parameter in real time during said process in response to a signal from said control system.

13. The method of claim 12 wherein said control system is programmed to store a predetermined reference parameter range; to receive said sensed parameter value and compare said sensed parameter value to said stored reference parameter range; to indicate acceptable anti-microbial processing conditions when said sensed parameter value is within said reference parameter range; and to change the value of the parameter when said sensed parameter value is outside said reference parameter range.

14. The method of claim 12 wherein said anti-microbial process is selected from the group consisting of decontamination, sterilization, disinfection, and sanitization.

15. A method of real-time monitoring and real-time controlling a parameter value in a simulated load during an anti-microbial processing cycle performed in a decontamination apparatus having a control system, the method comprising the steps of:
 (a) placing a challenge load-simulating device in said decontamination apparatus, said device comprising a semi-permeable barrier that is resistant to passage of a chlorine-based anti-microbial agent, a receiving area for the chlorine-based anti-microbial agent that passes said semi-permeable barrier; and a first sensor probe positioned in said receiving area for real-time sensing therein of a parameter value during the anti-microbial cycle;
 (b) exposing said challenge load-simulating device to said chlorine-based anti-microbial agent during said cycle;
 (c) sensing in real-time the parameter value within said receiving area of said challenge load-simulating device during said cycle;
 (d) transmitting in real-time the sensed parameter value in said challenge load-simulating device from said first sensor probe to said control system; and
 (e) controlling the value of at least one of temperature, pressure, relative humidity, and anti-microbial agent concentration in real time during the cycle in response to said sensed parameter value.

16. The method of claim 15, wherein said control system is programmed to store a predetermined reference parameter range; to compare said sensed parameter value to said stored reference parameter range; and to indicate acceptable anti-microbial processing conditions when said sensed parameter value is within said reference parameter range.

17. A method of monitoring and controlling a parameter value in real-time in a simulated load during an anti-microbial processing cycle performed in a decontamination apparatus having a control system, said control system being programmed to store a predetermined reference parameter range and to compare a sensed parameter value with said predetermined reference parameter range, said method comprising the steps of:
 (a) positioning a challenge load-simulating device in said decontamination apparatus, said device comprising a resistance barrier resistant to penetration of an anti-microbial agent, and a receiving area for the anti-microbial agent that flows past the resistance barrier;
 (b) disposing a first sensor probe within said device, such that said first sensor probe is positioned in said receiving area for real-time sensing therein of a parameter value during said cycle, said first sensor probe comprising a transmitting means for transmitting the sensed parameter value from said first sensor probe to said control system;

(c) exposing said load-simulating device during said cycle, to an anti-microbial agent selected from the group consisting essentially of steam, ethylene oxide gas, liquid hydrogen peroxide, vaporized hydrogen peroxide, liquid formaldehyde, vaporized formaldehyde, liquid peroxy compounds, vaporized peroxy compounds, ozone, ionized gases, plasmas, chlorine-based agents and combinations thereof;

(d) sensing in real time the parameter value within said receiving area of said device during said cycle;

(e) transmitting in real time the sensed parameter value in said load-simulating device from said first sensor probe to said control system; and (f) controlling the value of the parameter in real time during said cycle in response to a signal from said control system, said signal based upon a comparison of said sensed parameter value with said predetermined reference parameter range.

18. A method for monitoring and controlling an anti-microbial process in a decontamination chamber, the method comprising:

placing in the chamber a challenge load-simulating device comprising a perforated member that is resistant to penetration by an anti-microbial agent vapor, and a receiving area for receiving anti-microbial agent vapor that penetrates the perforated member;

conducting an anti-microbial processing cycle in the chamber;

sensing in real-time the concentration of the agent vapor in the receiving area during the cycle and generating an electronic parameter value in response thereto; and, controlling at least one of vapor concentration, chamber temperature, and cycle duration in real-time in response to the sensed real-time parameter value.

19. The method of claim 18 wherein said anti-microbial process is selected from the group consisting of a decontamination process, a sterilization process, a disinfection process, and a sanitization process.

20. A method of monitoring an anti-microbial processing parameter in a decontamination system including a sensor which (i) measures said parameter and (ii) provides a real-time control signal representative of said parameter, said method comprising:

selecting a resistance barrier to simulate the barrier encountered by an anti-microbial agent when penetrating a load, said resistance barrier including a series of baffles that define a tortuous path;

disposing said resistance barrier between said sensor and said agent; and monitoring in real-time said control signal provided by said sensor.

* * * * *